United States Patent [19]
Ahluwalia et al.

[11] Patent Number: 5,455,234
[45] Date of Patent: Oct. 3, 1995

[54] INHIBITION OF HAIR GROWTH

[76] Inventors: Gurpreet S. Ahluwalia, 8632 Stable View Ct., Gaithersburg, Md. 20879; Douglas Shander, 16112 Howard Landing Dr., Gaithersburg, Md. 20878

[21] Appl. No.: 213,954

[22] Filed: Mar. 16, 1994

[51] Int. Cl.$^6$ .......................... A61K 31/70; A61K 31/44; A61K 31/195; A61K 31/24
[52] U.S. Cl. .................. 514/46; 514/50; 514/303; 514/354; 514/534; 514/561; 536/27.13; 536/27.22; 536/27.30; 536/27.31; 536/27.60; 536/28.30; 546/118; 546/324; 560/171; 562/503; 562/504; 562/505; 562/556; 562/559; 562/564; 562/574; 562/588
[58] Field of Search .................. 514/46, 50, 303, 514/354, 547, 561, 564, 534

[56] References Cited

U.S. PATENT DOCUMENTS

| | | | |
|---|---|---|---|
| 2,726,983 | 12/1955 | Yale et al. | 514/354 |
| 3,426,137 | 2/1969 | Philpitt et al. | 424/330 |
| 4,039,669 | 8/1977 | Beyler et al. | 424/243 |
| 4,082,846 | 4/1978 | Clark | 424/266 |
| 4,139,638 | 2/1979 | Neri et al. | 424/324 |
| 4,161,540 | 7/1979 | Neri et al. | 424/324 |
| 4,191,775 | 3/1980 | Glen | 424/304 |
| 4,269,831 | 5/1981 | Ferrari et al. | 424/241 |
| 4,344,941 | 8/1982 | Wiechert et al. | 424/243 |
| 4,370,315 | 1/1983 | Greff et al. | 424/94 |
| 4,439,432 | 3/1984 | Peat | 424/240 |
| 4,720,489 | 1/1988 | Shander | 514/171 |
| 4,885,289 | 12/1989 | Breuer et al. | 514/170 |
| 4,937,234 | 6/1990 | Fahim | 514/53 |
| 5,095,007 | 3/1992 | Ahluwalia | 514/23 |
| 5,096,911 | 3/1992 | Ahluwalia et al. | 514/380 |
| 5,132,293 | 7/1992 | Shander et al. | 514/46 |
| 5,143,925 | 9/1992 | Shander et al. | 514/378 |
| 5,189,212 | 2/1993 | Ruenitz | 562/468 |
| 5,271,942 | 12/1993 | Heverhagen | 424/451 |
| 5,300,284 | 4/1994 | Wiechers et al. | 424/70 |

FOREIGN PATENT DOCUMENTS

| | | | |
|---|---|---|---|
| 0157000 | 1/1953 | Australia | 514/354 |
| 0008658 | 3/1980 | European Pat. Off. | 514/561 |
| 0532219A2 | 3/1993 | European Pat. Off. | |
| 2450247 | 9/1980 | France | 514/561 |
| 4342516 | 11/1992 | Japan | 514/561 |
| 0967133 | 8/1964 | United Kingdom | 514/354 |
| 1387769 | 3/1975 | United Kingdom | 514/564 |
| 1458349 | 12/1976 | United Kingdom | |
| 2058052 | 4/1981 | United Kingdom | 514/561 |
| 2078735 | 1/1982 | United Kingdom | 514/561 |

OTHER PUBLICATIONS

Reis et al., "Investigation of Some Amino Acid Analogs and Metabolites as Inhibitors of Wool and Hair Growth," *Aust. J. Biol. Sci.*, 36(2), 157–170 (1983); *Chem. Abstr.*, 99(9), p. 486, Abstr. No. 68955q (1983).
Lucky et al., "Hair Follicle Response of the Golden Syrian Hamster Flank Organ to Continuous Testosterone Stimulation Using Silastic Capsules," *J. Investigative Dermatology*, 86(1), 83–86 (1986).
Goos et al., "An Improved Method of Evaluating Antiandrogens," *Arch. Dermatol. Res.*, 273, 333–341 (1982).
Messenger, "The Control of Hair Growth: An Overview," *J. Investigative Dermatology*, 101(1), Supplement, 4S–9S (1993).
Sato, "The Hair Cycle and Its Control Mechanism," in *Biology and Disease of the Hair*, Kobori et al. eds., University Park Press, Baltimore, Md., 1975, pp. 3–13.
Simpson et al., "The Effect of Topically Applied Progesterone on Sebum Excretion Rate," *British J. Dermatology*, 100, 687–692 (1979).
Burdick et al., "The Topical Effect of the Antiandrogen Chlormadinone Acetate and Some of Its Chemical Modifications on the Hamster Costovertebral Organ," *British J. Dermatology*, 82(Supplement 6), 19–25 (1970).
Girard et al., "Inhibition of Testosterone Metabolism and Lipogenesis in Animal Sebaceous Glands by Progesterone," *Arch. Dermatol. Res.*, 269, 281–290 (1980).
Champion, "Therapeutic Use of the Non-Steroidal and Anti-Inflammatory Drugs," *Medical J. Australia*, 149(4), 203–213 (1988).
Uren et al., "Modulation of Cysteine Metabolism in Mice—Effects of Propargylglycine and L-Cyst(e)ine–Degrading Enzymes," *Biochemical Pharmacology*, 27(24), 2807–2814 (1978).
Washtien et al., "Mechanism of Inactivation of $\gamma$-Cystathionase by the Acetylenic Substrate Analogue Propargylglycine," *Biochemistry*, 16(11), 2485–2490 (1977).
Chiang et al., "S-Adenosyl-L-homocysteine Hydrolase: Analogues of S-Adenosyl-L-homocysteine as Potential Inhibitors," *Molecular Pharmacology*, 13, 939–947 (1977).
Glazer et al., "3-Deazaneplanocin-A: A New Inhibitor of S-Adenosylhomocyteine Synthesis and Its Effects in Human Colon Carcinoma Cells," *Biochemical Pharmacology*, 35(24), 4523–4527 (1986).
Porter et al., "Growth Inhibition by Methionine Analogue Inhibitors of S-Adenosylmethionine Biosynthesis in the Absence of Polyamine Depletion," *Biochem. Biophys. Res. Comm.*, 122(1), 350–357 (1984).
Slavik et al., "Changes in Serum and Urine Amino Acids in Patients with Progressive Systemic Sclerosis Treated with 6-Azauridine Triacetate," *Biochemical Pharmacology*, 22(11), 1295–1300 (1973).
Guggenheim et al., "Cystathionine $\gamma$-Synthase from Salmonella," *J. Biol. Chem.*, 244(13), 3722–3727 (1969).
Silverman et al., "Mechanism of Inactivation of +97-Cystathionase by $\beta$, +62, $\beta$–Trifluoroalanine," *Biochemistry*, 16(25), 5515–5520 (1977).
Greenberg, "Biosynthesis of Cysteine and Cystine," Ch. 12 in *Metabolic Pathways*, 3rd. Ed., vol. 7, Academic Press, New York, Greenberg ed., 1975, pp. 505–528.
O'Donnel et al., "Assay of Ornithine Aminotransferase by High-Performance Liquid Chromatography," *Analytical Biochemistry*, 90, 41–46 (1978).

*Primary Examiner*—Douglas W. Robinson
*Assistant Examiner*—L. Eric Crane
*Attorney, Agent, or Firm*—Fish & Richardson

[57] ABSTRACT

Mammalian hair growth is reduced by applying to the skin an inhibitor of a cysteine synthetic pathway enzyme.

35 Claims, No Drawings

INHIBITION OF HAIR GROWTH

The invention relates to a method of the inhibition of unwanted hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; Shander et al., U.S. Pat. No. 5,132,293; and Shander et al., U.S. Pat. No. 5,143,925.

Cysteine is synthesized in cells from methionine according to the following biochemical pathway:

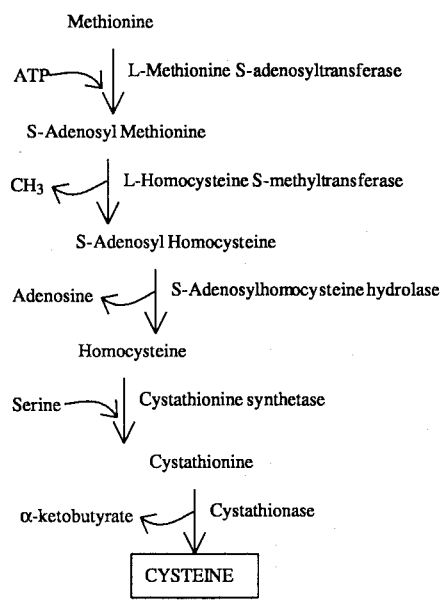

In the initial step in the pathway, L-methionine S-adenosyltransferase converts L-methionine to S-adenosyl methionine by transferring the adenosyl moiety of ATP to L-methionine. In the second step, L-homocysteine S-methyltransferase converts the S-adenosyl methionine to S-adenosyl-L-homocysteine by transferring the methyl group of S-adenosyl methionine to an acceptor molecule present in the cell. Next, S-adenosyl homocysteine hydrolase (adenosylhomocysteinase) converts the S-adenosyl-L-homocysteine to L-homocysteine, releasing adenosine in the process. Then, cystathionine synthase catalyzes the condensation of the L-homocysteine with L-serine to form L-cystathionine. Finally, cystathionase (cystathionine gamma-lyase) hydrolyzes the L-cystathionine to form L-cysteine.

The enzymes in the biochemical pathway described above will be referred to herein as the "cysteine synthetic pathway enzymes." It has now been found that unwanted mammalian (including human) hair growth—particularly androgen-stimulated hair growth—can be inhibited by applying to the skin a composition including an inhibitor of a cysteine synthetic pathway enzyme in an amount effective to reduce hair growth. The unwanted hair growth which is reduced may be normal hair growth, or hair growth that results from an abnormal or diseased condition.

Among the inhibitors that can be used are inhibitors of L-methionine S-adenosyltransferase such as cycloleucine, selomethionine, L-2-amino-4-methoxy-cis-but-3-enoic acid, and 2-aminobicyclo [2.1.1]hexane-2-carboxylic acid; inhibitors of S-adenosyl homocysteine hydrolase such as 3-deazaneplanocin, adenosine-5'-carboxaldehyde, 3-deazaadenosine, and S-3-deazaadenosyl-L-homocysteine; inhibitors of cystathionine synthase such as isonicotinicacid hydrazide, O-succinyl serine, adenosine, and 6-azauridine-2',3',5'-triacetate; and inhibitors of cystathionase such as D,L-2-amino-4-pentynoic acid (D,L-propargylglycine), $\beta,\beta$-dichloro-D,L-alanine, $\beta,\beta,\beta$-trifluoroalanine, and L-aminoethoxyvinylglycine. All of these compounds are known and most are commercially available. Irreversible inhibitors are preferred; reversible inhibitors (competitive and non-competitive) can also be used.

The inhibitors of a cysteine synthetic pathway enzyme preferably are incorporated in a topical composition which preferably includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US93/0506A. In addition, a penetration enhancer may be added to the vehicle to further enhance the effectiveness of the formulation.

The concentration of the inhibitor in the composition may be varied over a wide range up to a saturated solution, preferably from 0.1% to 30% by weight or even more; the reduction of hair growth increases as the amount of inhibitor applied increases per unit area of skin. The maximum amount effectively applied is limited only by the rate at which the inhibitor penetrates the skin. Generally, the effective amounts range from 100 to 3000 micrograms or more per square centimeter of skin.

The composition should be topically applied to a selected area of the body from which it is desired to inhibit hair growth. For example, the composition can be applied to the face, particularly to the beard area of the face, i.e., the cheek, neck, upper lip, and chin. The composition can also be applied to the legs, arms, torso or armpits. The composition is particularly suitable for inhibiting the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency or hair removal is reduced, or the subject perceives less hair on the treated site, or quantitatively, when the weight of hair removed by shaving (i.e., hair mass) is reduced.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a composition including an inhibitor, the flank organs of each of a group of hamsters are depilated by applying a thioglycolate based chemical depilatory (Surgex). To one organ of each animal 25 μl. of vehicle alone once a day is applied, while to the other organ of each animal an equal amount of vehicle containing an inhibitor of a cysteine synthetic pathway enzyme is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide an inhibition in hair growth of at least about 32%, more preferably at least about 50%, and most preferably at least about 70% when tested in the Golden Syrian hamster assay. A number of inhibitors of cysteine synthetic pathway enzymes were tested in the Golden Syrian hamster assay; the results are provided in Table 1.

Topical application of compositions including 3-deazaneplanocin demonstrate that an increased dosage level of the inhibitor provided an increased inhibition in hair growth. The results are provided in Table 2.

TABLE 2

| | Dose | Vehicle | pH | Hair Mass Treated (mg) | Hair Mass Control (mg) | Percent Inhibition (mean ± SEM) |
|---|---|---|---|---|---|---|
| 3-Deazaneplanocin | 0.25% | A | 4.5 | 1.889 ± 0.15 | 2.213 ± 0.08 | 14.82 ± 5.45 |
| 3-Deazaneplanocin | 0.50% | A | 5.0 | 1.487 ± 0.16 | 2.366 ± 0.26 | 35.49 ± 4.62 |
| 3-Deazaneplanocin | 1.00% | A | 5.0 | 1.113 ± 0.08 | 2.303 ± 0.11 | 50.94 ± 4.77 |
| 3-Deazaneplanocin | 5.00% | A | 5.0 | 0.357 ± 0.15 | 2.363 ± 0.35 | 86.65 ± 4.81 |

Hair follicles were isolated from the flank organs which were treated with either an inhibitor of a cysteine pathway enzyme or the carrier without the inhibitor (the control). L-Cystathiorine, homocysteine, and S-adenosyl homocysteine, which are involved in a pathway leading to cysteine synthesis, were measured by an amino acid analysis method. The amino analysis of hamster flank organ hair follicles was carried out using a commercially available system (Pico-Tag; Waters Associates, Inc., Milford, Mass.). Hair follicle amino acids were extracted with 0.1N HCL, an derivatized with phenylisothiocyanate to yield the phenylthiohydantion derivatives of the respective amino acids, which were then separated by C-18 reverse phase chromatography, and quantitated by in-line UV spectrophotometry.

More specifically, 250–500 μl of 0.1N HCL was added to each flank organ hair follicle sample, followed by treatment with a sonicator device to obtain cell extracts. The cell extracts were centrifuged at 12,000×g for 5 min, and the recovered supernatant was filtered through 0.45μ filter. The filtrate was vacuum dried under nitrogen using the Pico-Tag work station. Samples were then derivatized with phenylisothiocyanate reagent by the procedure described in the Waters Associates Pico-Tag manual. An aliquot of the derivatized sample was injected on a C-18 reverse phase column (Pico-Tag column) and the elution was carried out with a gradient buffer system. This procedure separated the amino acids L-cystathionine, homocysteine, and S-adenosyl

TABLE 1

| Inhibitor | Dose | Vehicle | pH | Hair Mass Treated (mg mean ± SEM) | Hair Mass Control (mg mean ± SEM) | Percent Inhibition (mean ± SEM) |
|---|---|---|---|---|---|---|
| 3-Deazaneplanocin | 5% | A | 4.5 | 0.357 ± 0.15 | 2.363 ± 0.35 | 86.65 ± 4.81 |
| 6-Azauridine-2',3',5'-triacetate | 20% | A | 7.0 | 0.455 ± 0.05 | 2.372 ± 0.14 | 80.25 ± 2.37 |
| O-Succinyl serine | 15% | A | 8.0 | 0.710 ± 0.07 | 2.043 ± 0.18 | 63.58 ± 4.69 |
| Adenosine | 10% | A | 4.5 | 1.140 ± 0.12 | 2.619 ± 0.24 | 55.28 ± 4.00 |
| Isonicotinic acid hydrazide | 20% | A | 8.5 | 1.344 ± 0.18 | 2.139 ± 0.22 | 35.13 ± 7.98 |
| DL-Propargylglycine | 15% | B | 9.5 | 1.401 ± 0.14 | 2.148 ± 0.19 | 33.12 ± 5.59 |
| 3,3,3,-Trifluoro-DL-alanine | 20% | A | 7.5 | 1.110 ± 0.13 | 1.681 ± 0.13 | 32.36 ± 8.01 |
| Isonicotinic acid hydrazide + DL-Propargylglycine | 10%+ 10% | B | 9.0 | 0.920 ± 0.29 | 2.385 ± 0.74 | 60.72 ± 4.69 |

Vehicle A: Pure water (68%), ethanol (16%), propylene glycol (5%), dipropylene glycol (5%), benzyl alcohol (4%), and propylene carbonate (2%)
Vehicle B: Pure water (73%), propylene glycol (20%), benzyl alcohol (5%), and N-methyl-2-pyrrolidone (2%)

homocysteine from other amino acids present in hair follicle extracts. The amino acid concentrations were determined at UV wavelength 254 nm using an in-line spectrophotometer and a dedicated HPLC control and data analysis system (Waters Associates). The results are provided in Table 3.

TABLE 3

| | Dose | Vehicle | pH | Percent of Untreated Control (100%) | | |
| --- | --- | --- | --- | --- | --- | --- |
| | | | | L-Cystathionine | Homocysteine | S-Adenosyl Homocysteine |
| Vehicle control | — | A | 4.5 | 100 | 100 | 100 |
| 3-Deazaneplanocin | 0.125% | A | 4.5 | 49 | — | 144 |
| 3-Deazaneplanocin | 0.250% | A | 4.5 | 29 | — | 149 |
| 3-Deazaneplanocin | 0.500% | A | 4.5 | 12 | — | 218 |
| 6-Azauridine-2',3',5'triacetate | 20% | A | 7.0 | 60 | — | — |
| O-Succinyl serine | 15% | A | 8.0 | 66 | 228 | — |

It will be appreciated by those skilled in the art that the invention can be performed within a wide range of equivalent parameters of composition and conditions without departing from the spirit or scope of the invention or of any embodiment thereof.

We claim:

1. A method of inhibiting mammalian hair growth which comprises selecting an area of skin from which reduced hair growth is desired; and applying to said area of skin an inhibitor of a cysteine pathway enzyme related to hair growth in an amount effective to reduce hair growth.

2. The method of claim 1, wherein said inhibitor is cycloleucine.

3. The method of claim 1, wherein said inhibitor is selenomethionine.

4. The method of claim 1, wherein said inhibitor is L-2-amino-4-methoxy-cis-but-3-enoic acid.

5. The method of claim 1, wherein said inhibitor is 2-aminobicyclo[2.1.1]hexane-2-carboxylic acid.

6. The method of claim 1, wherein said inhibitor is 3-deazaneplanocin.

7. The method of claim 1, wherein said inhibitor is adenosine-5'-carboxaldehyde.

8. The method of claim 1, wherein said inhibitor is 3-deazaadenosine.

9. The method of claim 1, wherein said inhibitor is S-3-deazaadenosyl-L-homocysteine.

10. The method of claim 1, wherein said inhibitor is isonicotinicacid hydrazide.

11. The method of claim 1, wherein said inhibitor is O-succinyl-serine.

12. The method of claim 1, wherein said inhibitor is 6-azauridine-2',3',5'-triacetate 13. The method of claim 1, wherein said inhibitor is adenosine.

14. The method of claim 1, wherein said inhibitor is D,L-2-amino-4-pentynoic acid.

15. The method of claim 1, wherein said inhibitor is β,β-dichloro-D,L-alanine.

16. The method of claim 1, wherein said inhibitor is β,β,β-trifluoroalanine.

17. The method of claim 1, wherein said inhibitor is L-aminoethoxyvinylglycine.

18. The method of claim 1, wherein said inhibitor is an inhibitor of L-methione S-adenosyltransferase.

19. The method of claim 1, wherein said inhibitor is an inhibitor of L-homocysteine S-methyltransferase.

20. The method of claim 1, wherein said inhibitor is an inhibitor of S-adenosyl homocysteine hydrolase.

21. The method of claim 1, wherein said inhibitor is an inhibitor of cystathionine synthase.

22. The method of claim 1, wherein said inhibitor is an inhibitor of cystathionase.

23. The method of claim 1, wherein said inhibitor is an irreversible inhibitor.

24. The method of claim 1, wherein said inhibitor is applied as part of a composition including a dermalogically acceptable vehicle.

25. The method of claim 24, wherein the concentration of said inhibitor of in said composition is between 1% and 30%.

26. The method of claim 24, wherein the composition provides a reduction in hair growth of at least 30% when tested in the Golden Syrian hamster assay.

27. The method of claim 24, wherein the composition provides a reduction in hair growth of at least 50% when tested in the Golden Syrian hamster assay.

28. The method of claim 24, wherein the composition provides a reduction in hair growth of at least 70% when tested in the Golden Syrian hamster assay.

29. The method of claim 1, wherein the inhibitor is applied to the skin in an amount of from 100 to 3000 micrograms of said inhibitor per square centimeter of skin.

30. The method of claim 1, wherein said mammal is a human.

31. The method of claim 23, wherein said area of skin is on the face of the human.

32. The method of claim 30, wherein said area of skin is on a leg of the human.

33. The method of claim 30, wherein said area of skin is on an arm of the human.

34. The method of claim 30, wherein said area of skin is in an armpit of the human.

35. The method of claim 30, wherein said area of skin in on the torso of the human.

* * * * *

UNITED STATES PATENT AND TRADEMARK OFFICE
CERTIFICATE OF CORRECTION

PATENT NO. : 5,455,234
DATED : October 3, 1995
INVENTOR(S) : Gurpreet S. Ahluwalia et al.

It is certified that error appears in the above-indentified patent and that said Letters Patent is hereby corrected as shown below:

On the title page, item [54] and column 1, line 2, after "GROWTH" insert --BY TOPICAL APPLICATION OF CERTAIN ENZYME INHIBITORS--.

TITLE PAGE

In the References Cited, Other Publications Section:

In the Silverman reference, "+97" should be --γ--;
In the Silverman reference, "+62" should be --β,β--.

Col. 4, line 27, "an" should be --a--.

Col. 5, Table 3, line 4, column 4 (pH column), "4.5" should be --5.0--.

In claim 31, line 1, "23" should be --30--.

Signed and Sealed this

Thirteenth Day of May, 1997

Attest:

BRUCE LEHMAN

Attesting Officer        Commissioner of Patents and Trademarks